(12) United States Patent
Kovac

(10) Patent No.: US 6,237,597 B1
(45) Date of Patent: May 29, 2001

(54) ENDOTRACHEAL MEDICATION PORT ADAPTER

(76) Inventor: JoAnn Kovac, 74-19 58th Ave, Elmhurst, NY (US) 11373

( * ) Notice: Subject to any disclaimer, the term of this patent is extended or adjusted under 35 U.S.C. 154(b) by 0 days.

(21) Appl. No.: 09/211,122

(22) Filed: Dec. 14, 1998

(51) Int. Cl.[7] .................................................. A61M 16/00
(52) U.S. Cl. ................................ 128/207.14; 128/203.12
(58) Field of Search ........................ 128/203.12, 203.14, 128/203.22, 203.28, 205.13, 205.17, 912, DIG. 26, 207.16, 207.29, 207.14, 207.15, 205.23, 202.22

(56) References Cited

U.S. PATENT DOCUMENTS

| | | |
|---|---|---|
| 3,667,475 * | 6/1972 | Venturelli et al. .................... 128/351 |
| 4,584,998 | 4/1986 | McGrail . |
| 4,669,463 | 6/1987 | McConnell . |
| 4,723,543 | 2/1988 | Beran . |
| 4,815,459 | 3/1989 | Beran . |
| 4,953,547 | 9/1990 | Poole . |
| 5,031,613 | 7/1991 | Smith et al. . |
| 5,078,131 | 1/1992 | Foley . |
| 5,143,062 | 9/1992 | Peckham . |
| 5,146,916 | 9/1992 | Catalini . |
| 5,181,508 | 1/1993 | Poole . |
| 5,197,463 | 3/1993 | Jeshuran . |
| 5,207,220 | 5/1993 | Long . |
| 5,605,147 * | 2/1997 | Truthan ........................... 128/203.12 |
| 5,720,282 * | 2/1998 | Wright ............................. 128/207.14 |
| 5,735,271 * | 4/1998 | Lorenzen et al. ............... 128/207.16 |
| 5,803,078 * | 9/1998 | Brauner .......................... 124/207.14 |
| 5,996,579 * | 12/1999 | Coates et al. ................... 128/205.13 |

* cited by examiner

Primary Examiner—Dennis Ruhl
Assistant Examiner—Teena Mitchell
(74) Attorney, Agent, or Firm—Michael I. Kroll

(57) ABSTRACT

An endotracheal medication port adapter for administering a first medication and one of a second medication and life supporting gas directly into the pulmonary vasculature of a patient is described by the present invention. The adapter includes a first medication tube including a first medication receiving end for receiving the first medication therethrough and a second end. A ring adapter includes a first tube receiving port for receiving the second end of the first medication tube, a depositing port and a second tube receiving port. The first tube receiving port receives the second end of the first medication tube, wherein the first medication tube extends through the first tube receiving port and the depositing port for dispensing medication deposited therein into the pulmonary vasculature of the patient. A flexible membrane including a recess therein is positioned to cover the second tube receiving port for receiving and forming an airtight seal with one of a second medication tube and a source of life supporting gas and a cover is positioned to seal the second tube receiving port when one of a second medication tube and a source of life supporting gas is not received by the flexible membrane.

5 Claims, 3 Drawing Sheets

ENDOTRACHEAL MEDICATION PORT ADAPTER

BACKGROUND OF THE INVENTION

1. Field of the Invention

The instant invention relates generally to endotracheal medication port adapters and, more specifically, to an endotracheal medication port adapter for the administration of medication via a respiratory pathway.

This invention further relates to an endotracheal medication port adapter used by paramedics, nurses, doctors, etc. to administer drugs and, more particularly, to devices for coupling endotracheal tubes to sources of life supporting gas such as air or oxygen and for allowing for the introduction of medicine while maintaining the supply of gas. This invention relates generally to the administration of medicine to the pulmonary vasculature for the pulmonary administration of pharmaceuticals via an endotracheal tube designed to allow metered administration of drugs without necessitating the interruption of mechanical pulmonary ventilation.

2. Description of the Prior Art

Conventional systems for tracheal intubation are employed routinely by health care professionals in hospital settings. The function of tracheal intubation is to provide mechanical assistance to patients to secure air passage and respiration function. Such mechanical assistance is effected by an endotracheal tube extending from a patients lungs to the exterior of the patient where it is coupled to a ventilation source for the administration of oxygen, air or other gasses. In hospital settings, where environmental conditions are excellent, intravenous administration of life-saving drugs is preferred even when a patient is being assisted by an endotracheal tube.

In pre-hospital settings, endotracheal tubes are also employed by paramedics, etc. Generally, the patient is a victim of an accident or another life-threatening medical emergency event that requires the assistance of a mechanical respiration apparatus to supplement abnormal respiration function. As in hospital settings, the preferred method of injecting life-saving drugs in emergency life-threatening situations is intravenous. Unfortunately, the use of intravenous injection of medication in a pre-hospital setting is not always secured by IV therapy. Hence, the alternative of intratracheal drug administration in life-threatening situations is gaining acceptance.

Current endotracheal respiration systems allow for intratracheal drug injections only after disconnecting the life supporting ventilation apparatus supplied with oxygen. There is thus a need for an endotracheal medication port adapter that allows for the introduction of life saving drugs while continuing the flow of life-supporting gasses such as air or oxygen.

Hospitals and health care providers of pre-hospital medicine are increasingly utilizing sterile instruments on a use-once, discard basis. This trend is due to the desire to reduce the transmission of nosocomial infection from one patient to another. Endotracheal medication port adapters are in the use-once, discard category.

The conventional endotracheal respiration system usually comprises at least two separate parts: the tube and a connector for coupling to a ventilation apparatus. The parts are manufactured individually and then assembled, tested and finally packaged in a sterile container. Accordingly, the cost of the materials and labor for an endotracheal respiration system that is used only once is relatively high.

The need thus exists for an endotracheal respiration system, that is convenient, inexpensive and allows for the introduction of medication without interrupting the flow of life supporting gasses and that can be manufactured with few parts, assembled, tested and packaged in a sterile container for use in hospitals and pre-hospital settings on a use-once, discard basis.

Numerous endotracheal devices have been provided in prior art For example, U.S. Pat. Nos. 4,584,998; 4,669,463; 4,723,543; 4,815,459; 4,953,547; 5,031,613; 5,143,062; 5,146,916; 5,181,508; 5,197,463 and 5,207,220 are all illustrative of such prior art. While these units may be suitable for the particular purpose to which they address, they would not be as suitable for the purposes of the present invention as heretofore described.

U.S. Pat. No. 4,584,998

Inventor: Thomas W. McGrail

Issued: Apr. 29,1986

A multi-purpose tracheal tube for use with high frequency ventilation. The tube is an endotracheal tube including up to three lumens, in addition to the primary lumen, which serve various functions to provide versatility in the treatment of patients. In cuffed tubes one of the lumens is used for inflating the cuff once the tube has been placed in the desired position in the trachea of the patient. Another lumen, referred to as the "insufflation lumen", is used to deliver oxygen or other gases by constant insufflation, intermittent jet ventilation or high frequency ventilation. The third lumen, when incorporated, is employed for monitoring and irrigation. The distal opening of the irrigation or monitoring lumen is located just inside the distal tip of the tube while the insufflation lumen opening is located rearwardly toward the proximal end of the tube relative to the irrigation or monitoring lumen opening.

U.S. Pat. No. 4,669,463

Inventor: Richard B. McConnell

Issued: Jun. 2, 1987

An improved endotracheal tube apparatus comprising an endotracheal tube unit and an injection site adjunct unit wherein the tube unit is provided with a primary endotracheal tube passageway in communication with a respirator, and a lumen side port formed in the wall of the primary tube passageway, wherein the lumen side port is in open fluid communication with the injection site adjunct unit and the interior of the passageway whereby liquid medicants may be introduced into the passageway.

U.S. Pat. Nos. 4,723,543 and 4,815,459

Inventor: Anthony V. Beran

Issued: Feb. 9, 1988 and Mar. 28, 1989

A connector for a respirator apparatus which is adapted to be inserted into the open stem of a respiratory Y-tube and connected to an endotracheal tube is provided. In one embodiment the connector is adapted to be used as a pressure measuring or gas sampling device and in another embodiment as a pneumotach for measuring the respiratory flow rate of a patient. The dead space commonly encountered in prior art connectors is substantially reduced and the likelihood of disconnection is reduced or eliminated. The connector permits gas measurement adjacent the patient and at a cross sectional flow are that approximate the inner diameter of the endotracheal tube.

U.S. Pat. No. 4,953,547

Inventor: Samuel E. Poole, Jr.

Issued: Sep. 4, 1990

An improved drug administering respiration endotracheal system which permits simultaneous multiple injection of life-saving medication into the lungs of the patient without interruption of the flow of life supporting gases. The system includes a connector with a linear axial passageway for gases and two separate medication injection ports adapted to receive a hypodermic needle and a medical syringe.

U.S. Pat. No. 5,031,613

Inventor: Roy D. Smith et al.

Issued: Jul. 16,1991

A nebulizing catheter and method for delivering a nebulized medication to a patient. The catheter includes an hour-glass shaped neck near its distal end and one or more perforations formed in the distal end. The fluid may be forced through the catheter by a syringe or other suitable means. The catheter is preferably used in conjunction with an endotracheal tube into which the catheter is inserted.

U.S. Pat. No. 5,078,131

Inventor: Martin P. Foley

Issued: Jan. 7, 1992

Apparatus is provided for injecting medication into a ventilator circuit. An elbow connects an endotracheal tube to the external ventilator circuit. A port in the elbow is connected to a flexible sheath leading to an actuator receiving an MDI canister. A catheter extends from the actuator substantially through the sheath to a position adjacent the elbow. When it is desired to inject medication, the actuator is moved to a position adjacent the elbow, thus projecting the discharge end of the catheter to a position within the endotracheal tube, but short of the open end thereof.

U.S. Pat. No. 5,143,062

Inventor: Keith A. Peckham

Issued: Sep. 1, 1992

The present invention relates to an endotracheal tube used for mechanical ventilation of a hospital patient, the endotracheal tube is useful in evacuating contaminated secretions that pool within the trachea above an inflatable cuff associated with the endotracheal tube. The endotracheal tube of the present invention comprises a double lumen through which air may be circulated, thus creating an indirect gentle suction through a suction eye communicating with the distal ends of the lumens, and located at a position proximal to the inflation cuff. This gentle indirect suction reduces the risk of damage to the tracheal mucosa, which often occurs when applying direct suction.

U.S. Pat. No. 5,146,916

Inventor: Angelo S. Catalani

Issued: Sep. 15, 1992

An endotracheal tube is equipped for delivering a drug externally of the tube. The endotracheal tube includes a tube body having proximal end and distal ends, and at least one flexible irrigation cannula extending along the endotracheal tube body to its distal end. An irrigation diffuser means is attached to the irrigation cannula for spraying a drug delivered through the irrigation cannula externally of the endotracheal tube body. The endotracheal tube is particularly intended for artificial ventilation in surgical operations and in intensive resuscitation treatments. It is useful for the repeated administration and readministration of drugs, for instance, of local anesthetics, anti-inflammatories and mucolytics in the course of intubation.

U.S. Pat. No. 5,181,508

Inventor: Samuel E. Poole, Jr.

Issued: Jan. 26, 1993

An improved drug administering endotracheal respiration system for administering vital life-saving drugs into the lungs of a victim while maintaining the flow of life supporting gas thereto via ventilation apparatus comprising in combination a gas supply; a tube for establishing gas flow exchange between the lungs of the victim and the gas supply, the tube having a proximal end and a distal end for insertion into the trachea of the victim; and a connector for coupling the proximal end of the tube to the gas supply, the connector being formed as a cylinder with a gas input end and a gas discharge end and a linear axial passageway therebetween, the connector having a hypodermic needle port adapted for receiving a hypodermic needle for injecting vital life-saving drugs in liquid form into the passageway and then into the distal end of the tube intermixed with the gas, the hypodermic needle port having a portion integrally formed with the connector and a portion separable therefrom, the syringe port having a portion integrally formed with the connector and a portion separable therefrom, the main axial passageway adapted for atomizing and intermixing of the flow of life-saving drugs with the life-supporting gas.

U.S. Pat. No. 5,197,463

Inventor: Winston R. Jeshuran

Issued: Mar. 30,1993

An adapter for delivering a tube to a patient by way of the adapter and an anesthesia mask includes a compressible seal core of separable sections which define a passageway for the tube when the sections are assembled. A body and a head of the adapter include seats for receiving the seal core with the passageway oriented for delivering the tube through the adapter by way of an opening in the head. The seal core is adjustably compressed by the seats to form an adjustable seal around the tube. The openings in the head and body of the adapter for the tube are larger in diameter than the back of the tube, and can be removed completely from the tube over the back end of the tube.

U.S. Pat. No. 5,207,220

Inventor: Walker A. Long

Issued: May 4,1993

A method of administering a liquid pharmaceutical formulation, particularly a surfactant formulation, to at least one lung of a subject in need of such treatment is disclosed. The method is carried out while the subject has a breathing tube extending through the subject's mouth and larynx, and while ventilating at least one lung of the subject through the breathing tube. The method comprises simultaneously administering the liquid pharmaceutical formulation down the breathing tube and into at least one lung of the subject and ventilating at least one lung of the subject through the breathing tube. The method may be performed on premature infants to combat respiratory distress syndrome. A preferred apparatus for carrying out the method of the present invention comprises a breathing tube configured for insertion through a subject's mouth and larynx, a ventilating apparatus operatively associated with the breathing tube, and an injecting device such as a syringe operatively associated with the breathing tube for introducing a liquid pharmaceutical formulation into the breathing tube.

SUMMARY OF THE INVENTION

The instant invention relates generally to endotracheal medication port adapters and, more specifically, to an endotracheal medication port adapter for the administration of medication and/or oxygen via a respiratory pathway.

This invention further relates to an endotracheal medication port adapter used by paramedics, nurses, doctors, etc. to administer drugs and, more particularly, to devices for coupling an endotracheal tube to both sources of life supporting gas such as air or oxygen and pharmaceuticals concurrently for administering to the respiratory pathway. Thus, the pulmonary administration of pharmaceuticals via an endotracheal tube designed to allow metered administration of drugs is accomplished without interruption of mechanical pulmonary ventilation.

A primary object of the present invention is to provide an endotracheal medication port adapter that will overcome the shortcomings of the prior art devices.

A further object of the present invention to provide an endotracheal medication port adapter which allows injection of life saving medication into a victim's lungs without interrupting the delivery of oxygen via the ventilation apparatus.

It is a further object of the present invention is to provide an endotracheal medication port adapter constructed of relatively few parts and low cost materials which are easily fabricated, assembled, tested, and packaged in an individual sterile container for use in a use-once, discard setting.

It is a still further object of the present invention to provide an endotracheal medication port adapter capable of simultaneously delivering multiple life saving medications usually required in life threatening emergency settings such as valium for seizures, atropine for organo phosphate poisoning and/or bradyarrhythmias, epinephrine 1:10,000 for cardiac arrest, adreline 1:1,000 for anaphylaxis, lidocaine for arrhythmias and narcan for narcotic overdose, etc. to a patient.

A still further object of the present invention to provide an endotracheal medication port adapter including a flexible airtight seal about at least one port for attachment to either a source of life supporting gas, a source of medication or neither while supplying medication through the other port It is a further object of the present invention to provide an endotracheal medication port adapter able to atomize medicinal fluids in a flow of gas for delivery to a patient's lungs.

A still further object of the present invention is to provide an endotracheal medication port adapter not limited to only one mode of delivery, e.g. the choice of the life saving medication should not be limited by the present methods and apparatus.

A further object of the present invention is to provide an endotracheal medication port adapter which can be permanently attached to the end of a bag-valve mask (BVM) or endotracheal tube (ET).

An additional object of the present invention is to provide an endotracheal medication port adapter able to administer medications via a respiratory pathway through a ring shaped adapter wherein the medication port protrudes through the skin of the patient An even further object of the present invention is to provide an endotracheal medication port adapter that is simple and easy to use.

A still further object of the present invention is to provide an endotracheal medication port adapter that is economical in cost to manufacture.

Further objects of the invention will appear as the description proceeds.

An endotracheal medication port adapter for administering a first medication and one of a second medication and life supporting gas directly into the pulmonary vasculature of a patient is described by the present invention. The adapter includes a first medication tube including a first medication receiving end for receiving the first medication therethrough and a second end. A ring adapter includes a first tube receiving port for receiving the second end of the first medication tube, a depositing port and a second tube receiving port The first tube receiving port receives the second end of the first medication tube, wherein the first medication tube extends through the first tube receiving port and the depositing port for dispensing medication deposited therein into the pulmonary vasculature of the patient A flexible membrane including a recess therein is positioned to cover the second tube receiving port for receiving and forming an airtight seal with one of a second medication tube and a source of life supporting gas and a cover is positioned to seal the second tube receiving port when one of a second medication tube and a source of life supporting gas is not received by the flexible membrane.

In accordance with this invention, the endotracheal medication port adapter which may include one or more separate passageways, apart from an air passageway, is inserted into the trachea or a respiratory pathway of the patient and held in place. A passageway is connected to a puncturable member, e.g., a syringe receptor, and, with the endotracheal tube in place, medication is administered from a syringe with a hypodermic needle wherein first the needle of the syringe punctures the syringe receptor, and then the syringe pump is operated to force medication through a discrete passageway or passageways and into the lungs in a single and immediate operation.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENTS

Figure 1:
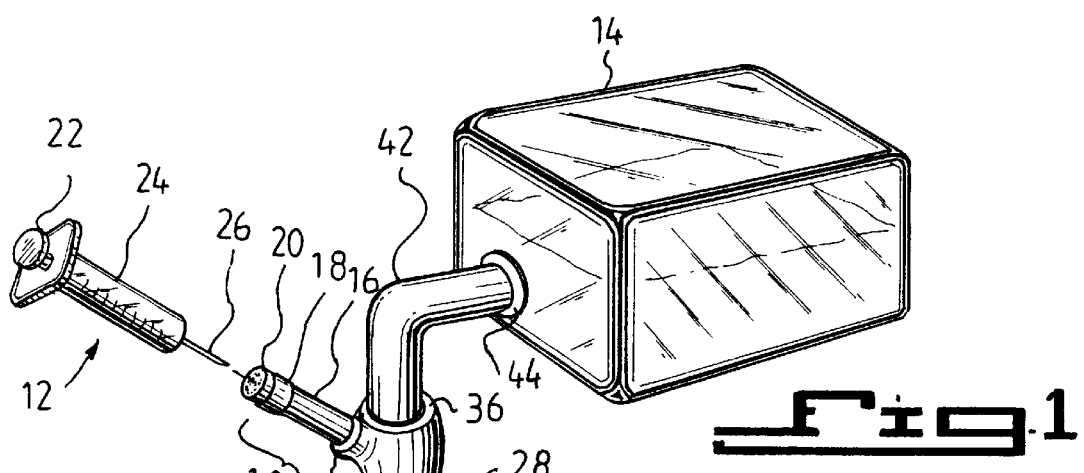
FIG. 1 is a perspective view of the endotracheal medication port adapter (EMPA) attached to the end of a bag valve mask and endotracheal tube.
Figure 2:
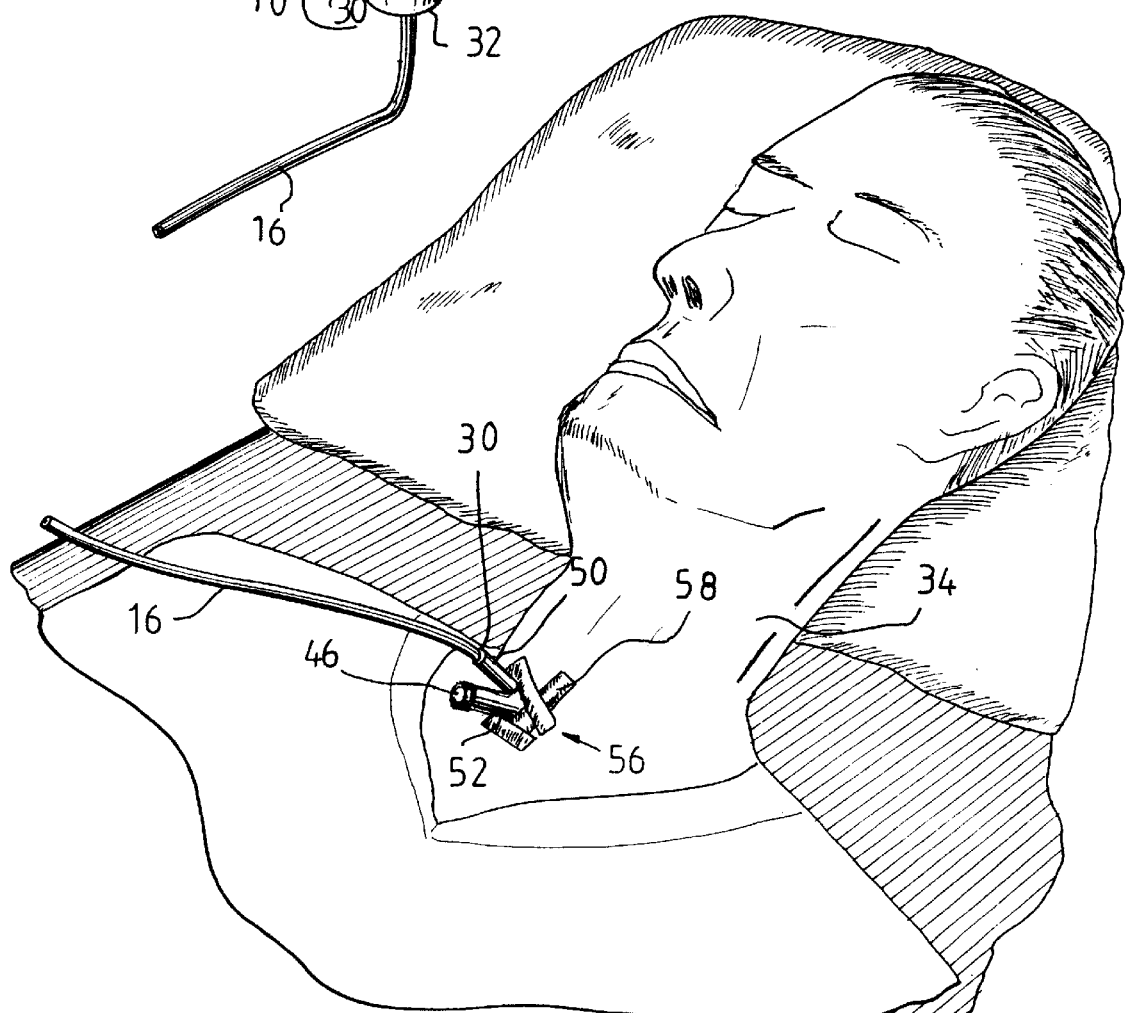
FIG. 2 is a perspective view of a patient with the endotracheal medication port adapter (EMPA) inserted through an incision of the trachea.
Figure 3:
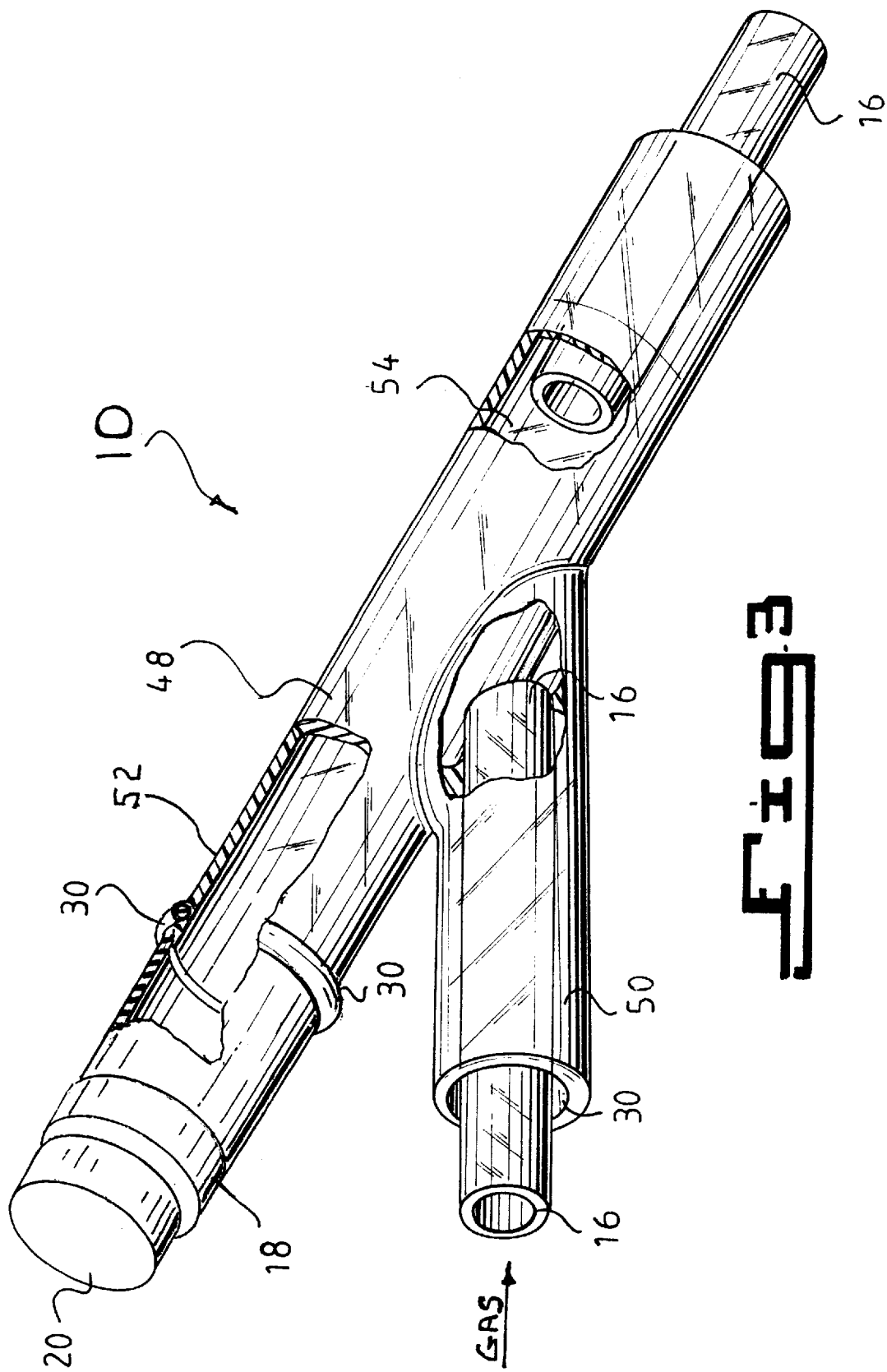
FIG. 3 is a top perspective view in partial cross-section of the endotracheal medication port adapter (EMPA)of the present invention.

Turning now descriptively to the drawings, in which similar reference characters denote similar elements throughout the several views, FIGS. 1 through 3 illustrate an endotracheal medication port adapter (EMPA) indicated generally by the numeral 10 connected to a syringe 12 and a bag valve mask 14.

The endotracheal medication port adapter 10 is designed for connection to both the syringe 12 for the delivery of medication to the pulmonary vasculature of a patient and to one of a second syringe, a source of life supporting gas, e.g. a bag valve mask 14, such as oxygen or neither. The endotracheal medication port adapter 10 includes a first medication receiving tube 48 having a medication port receptor 18 positioned at the distal end thereof for receiving the medication therethrough. A medication port stopper 20 is inserted into the medication port receptor 18. The syringe 12 includes a syringe plunger 22, a medication retaining tube 24 and a needle portion 26. The needle portion 26 is inserted into and received by the medication port stopper 20 to deliver medication therethrough and into the first medication receiving tube 16.

The first medication receiving tube 16 is connected at an end opposite the medication port stopper 20 to a ring adapter 28. The ring adapter 28 includes a first medication tube receiving port 30 for receiving the first medication receiving tube 16 and an endotracheal depositing port 32 for mating with the pulmonary vasculature of the patient 34. The first medication receiving tube 16 extends through the first medication tube receiving port 30, the ring adapter 28 and the endotracheal depositing port 32 for ultimately extending into the pulmonary vasculature of the patient 34 as is illustrated in FIG. 2. The ring adapter 28 further includes a second medication tube receiving port 36. The second medication tube receiving port 36 includes a flexible membrane 38 for receiving either a second medication receiving tube, the source of life supporting gas 14 or neither.

Figure 4:
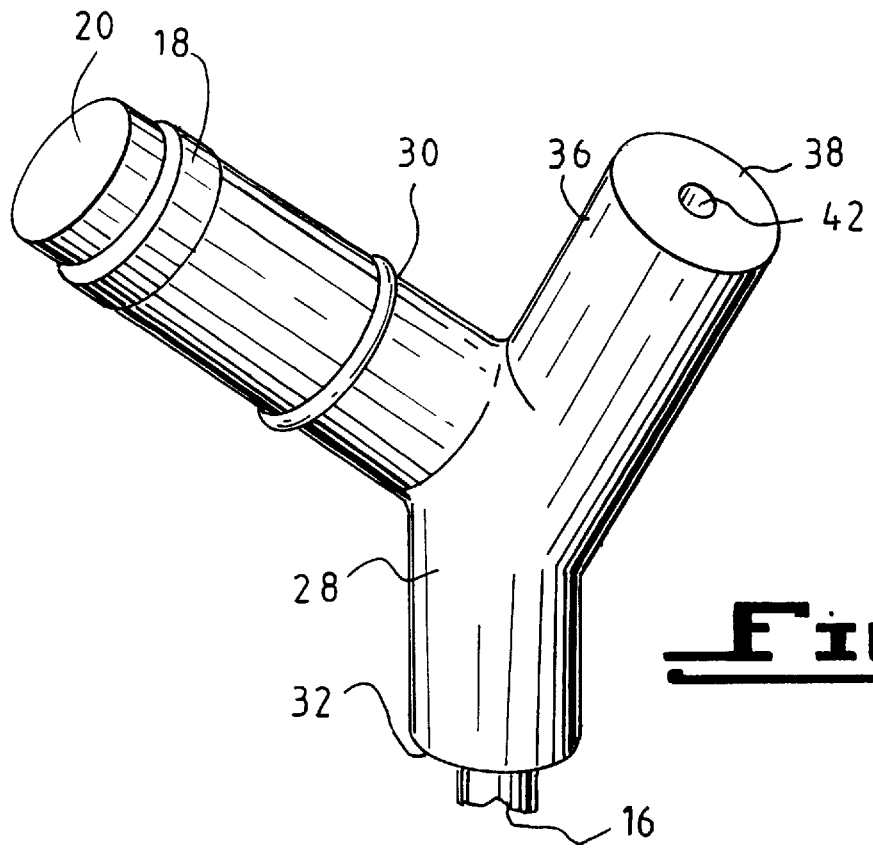
FIG. 4 is a top perspective view of the endotracheal medication port adapter (EMPA) of the present invention showing the flexible membrane.
Figure 5:
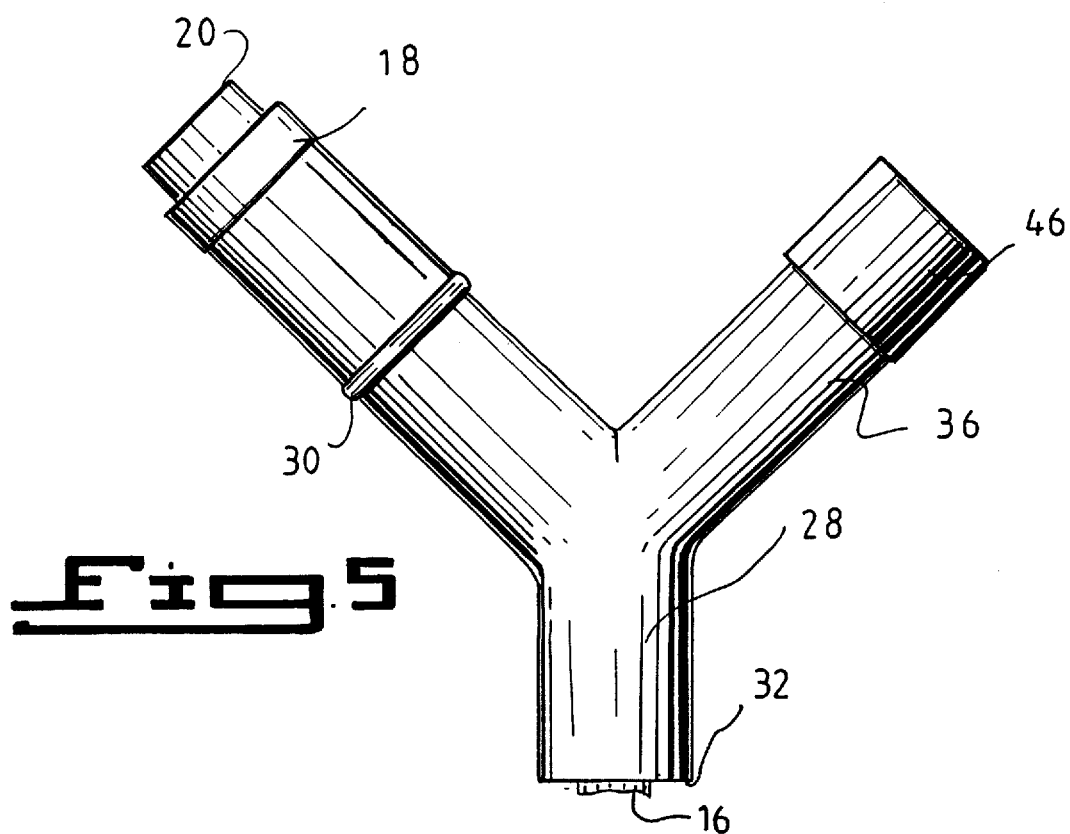
FIG. 5 is a top perspective view of the endotracheal medication port adapter (EMPA) of the present invention showing the cover for sealing the second passageway closed.

The second medication tube receiving port 36 is more clearly illustrated in FIGS. 4 and 5. As can be seen from these figures, the second medication tube receiving port 36 includes the flexible membrane 38. The flexible membrane 38 includes a recess 40 extending therethrough for receiving either the second medication receiving tube or a tube 42, e.g. bag valve mask tube for connecting to the bag valve mask 14. The bag valve mask 14 of FIG. 1 is connected to the endotracheal medication port adapter (EMPA) 10 by a bag valve mask tube connector 44 which is rigidly connected to the bag valve mask tube 42. The bag valve mask tube is inserted into and forms a seal with the flexible membrane 38. If neither the bag valve mask 14 or a second medication receiving tube is desired to be connected to the second receiving port 36, a cover 46 is used to seal the second receiving port 36 closed. When either the bag valve mask 14 or a second medication receiving tube is inserted into the second receiving port 36, the flexible membrane 38 forms an airtight seal therearound to prevent leakage of any substance therethrough.

FIG. 3 illustrates the endotracheal medication port adapter (EMPA) 10 in greater detail. The endotracheal medication port adapter (EMPA) 10 includes an endotracheal medication port tube 48 which consists of a first medication tube receptor 50 connecting the first medication tube receiving port 30 to the endotracheal medication port tube 48 and a second tube receptor 52 connecting the second medication port 30 to the endotracheal medication port tube 48. The first medication tube 16 extends into the first medication tube receptor 50 forming a water and air tight seal with the first medication tube receiving port 30. The first medication tube 16 then extends through the inside of the endotracheal medication port tube 54 for insertion into the pulmonary vasculature of the patient 34. The circumference of the first medication tube 16 is less than that of the endotracheal medication port tube 48 allowing any substance, medication or life supporting gas, to flow through the endotracheal medication port tube 48 around the first medication tube 16 and into the pulmonary vasculature of the patient 34.

The endotracheal medication port adapter 10 is inserted through an endotracheal incision 56 affixed to the patient 34 by surgical tape 58 as illustrated in FIG. 2. Medications are inserted via the syringe 12 through the endotracheal medication port stopper 20 without interruption. If it is desired to insert medication or life supporting gas through the second medication tube receptor 52 then the cover 46 must be removed and the proper tube inserted through the flexible membrane. For medications a second medication tube is inserted and for life supporting gas a device such as the bag valve mask tube 42 is inserted. The medication or life supporting gas flows into and through the endotracheal medication port tube 48 around the first medication tube 16 and into the pulmonary vasculature of the patient 34.

The adapter of the present invention is preferably composed of plastic material, the plastic material being transparent material to facilitate the monitoring of medication therethrough. The material composing the adapter should also be a heat sterilizable material capable of withstanding autoclaving and thus can be strilized providing for reusing. The first medication receptor tube should include a distal end receiving the medication port stopper which is preferably composed of a rubber-like material allowing for expansion and forming an airtight seal therewith.

From the above description it can be seen that the endotracheal medication port adapter of the present invention is able to overcome the shortcomings of prior art devices by providing an endotracheal medication port adapter which allows injection of life saving medication into the victim's lungs without interrupting the deliver of oxygen via the ventilation apparatus and is constructed of relatively few parts and low cost materials which are easily fabricated, assembled, tested, and packaged in an individual sterile container for use in a use-once, discard setting. The endotracheal medication port adapter is capable of simultaneously delivering multiple life saving medication injection usually found in life threatening emergency settings such as valium for seizures, atropine for organo phosphate poisoning and/or bradyarrhythmias, epinephrine 1:10,000 for cardiac arrest, adreline 1:1,000 for anaphylaxis, lidocaine for arrhythmias and narcan for narcotic overdose, etc. to a patient and atomizing medicinal fluids in a flow of gas for delivery to a patient's lungs. The endotracheal medication port adapter is also not limited to only one mode of delivery, e.g., the choice of the life saving medication should not be limited by the present methods and apparatus and is able to be permanently attached to the end of a bag-valve mask (BVM) or endotracheal tube (ET). Medications may also be administered via a respiratory pathway through a ring shaped adapter wherein the medication port protrudes through the skin of the patient by the endotracheal medication port adapter of the present invention. Furthermore, the endotracheal medication port adapter of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so filly reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letter Patent is set forth in the appended claims:

1. An endotracheal medication port adapter for administering, and in combination with, a first medication and a life supporting gas directly into the pulmonary vasculature of a patient, said adapter comprising:
   a) a first straight medication tube including a first end for receiving the first medication therethrough in liquid form and a second end adapted to deliver the liquid medication into the pulmonary vasculature of a patient, and syringe receptor means connected to said first end for receiving a syringe needle to deliver said liquid medication into said first medication tube;
   b) a second medication tube extending into and through said first medication tube having a first end outside of said first medication tube for receiving life supporting gas and a second end extending out of the second end of said first medication tube adapted to deliver said life supporting gas into the pulmonary vasculature of the patient;
   c) said second medication tube entering said first medication tube through a side thereof from a source of life supporting gas; and
   d) said second medication tube having a circumference smaller than a circumference of said first medication tube and concentric with and spaced from said first medication tube, wherein said liquid medication travels around said second medication tube into the pulmonary vasculature of the patient.

2. An endotracheal medication port adaptor as described in claim 1, whereas said adaptor has a Y-shaped configuration for facilitating atomization of liquid medication disposed through said first medication tube with said life supporting gas delivered through said second medication tube.

3. An endotracheal medication port adaptor as described in claim 1, wherein said adaptor is composed of plastic material.

4. An endotracheal medication port adapter as described in claim 1, whereas said adapter is composed of a heat sterilizable material capable of withstanding autoclaving.

5. An endotracheal medication port adapter as described in claim 1, whereas said adapter is composed of a transparent material to facilitate the monitoring of medication therethrough.

* * * * *